(12) United States Patent
Bowman et al.

(10) Patent No.: US 6,644,316 B2
(45) Date of Patent: Nov. 11, 2003

(54) VARIABLE APERTURE VENTING FOR RESPIRATORY MASK

(75) Inventors: Bruce R. Bowman, Eden Prairie, MN (US); Gary L. Hansen, Eden Prairie, MN (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/416,648

(22) Filed: Oct. 12, 1999

(65) Prior Publication Data

US 2003/0000532 A1 Jan. 2, 2003

(51) Int. Cl.$^7$ ................................................ A62B 18/10
(52) U.S. Cl. ........................ 128/207.12; 128/206.28; 128/206.12; 128/205.24
(58) Field of Search ................... 128/206.28, 204.24, 128/204.23, 204.18, 205.25, 205.24, 207.13, 207.12, 204.26, 205.23, 206.12

(56) References Cited

U.S. PATENT DOCUMENTS

| RE35,339 E | | 10/1996 | Rapaport | |
|---|---|---|---|---|
| 5,657,752 A | * | 8/1997 | Landis et al. | 128/201.28 |
| 5,857,460 A | * | 1/1999 | Popitz | 128/206.21 |
| 5,937,855 A | | 8/1999 | Zdrojkowski et al. | |
| 6,192,876 B1 | * | 2/2001 | Denyer et al. | 128/205.25 |

FOREIGN PATENT DOCUMENTS

| EP | 0 601 708 A2 | 6/1994 |
|---|---|---|
| FR | 2 695 320 A1 | 3/1994 |
| WO | WO 99/21602 A | 5/1999 |

* cited by examiner

*Primary Examiner*—Weilun Lo
*Assistant Examiner*—Darwin P Erezo
(74) *Attorney, Agent, or Firm*—Rothwell, Figg, Ernst & Manbeck PC

(57) ABSTRACT

A respiratory mask having a variable flow venting is provided according to the invention, including a gas supply hose, a mask shell adapted to output a gas to a respiratory system of a person, the mask shell adapted to be connected to the gas supply hose, and an exhaust gas flow volume regulating device which maintains a substantially constant gas flow volume out of the respiratory mask independent of an internal gas pressure inside the respiratory mask.

20 Claims, 4 Drawing Sheets

VARIABLE APERTURE VENTING FOR RESPIRATORY MASK

BACKGROUND OF THE INVENTION

1. Field of the Invention

The present invention relates generally to the field of respiratory masks.

2. Description of the Background Art

A respiratory mask is a device used to deliver a gas or gases to a person. FIG. 1 shows a respiratory mask 100 of the related art. The respiratory mask 100 includes a mask shell 104, a gas supply hose 107, a vent aperture 112, and an optional gasket 115. The mask shell 104 is fitted over a face of the person in order to supply a gas to a respiratory system of the person.

The respiratory mask 100 may be used to deliver any variety of gases, including air or oxygen, and a variety of medicines or treatments. Preferably, the mask shell does not allow a supplied gas to escape. A strap or other attaching means may be affixed to the mask shell and may be fitted over the head of the person. Constant pressure gas is therefore delivered, with the vent aperture 112 maintaining a substantially constant pressure in the mask. This is referred to as a continuous positive airway pressure (CPAP) mask. The vent aperture 112 allows expired carbon dioxide to escape from the mask. It is important that the vent aperture 112 be of a sufficient size to exhaust substantially all expired carbon dioxide under normal conditions of use.

In the related art, the need for venting has meant simply an aperture on or close to the mask shell, whereby exhaled air is flushed out of the respiratory mask by the positive pressure generated by the gas supply hose. This is taught by Rapaport U.S. Pat. No. Re. 35,339.

Several drawbacks exist with the venting of the related art respiratory mask 100. First, the air circulation within the mask 100 and vent aperture 112 may create annoying noises. Second, a jet of air from the vent aperture 112 may impinge on the wearer or on nearby persons. This can be seen in FIG. 1, where the vent aperture 112 and a resulting air jet are relatively close to the face of the wearer, and will in all likelihood be in the region of persons near to or sleeping with the wearer. As a result, these drawbacks may affect compliance with a therapy.

Therefore, there remains a need in the art for an improved respiratory mask.

SUMMARY OF THE INVENTION

A respiratory mask having a variable flow venting is provided according to the invention, comprising a gas supply hose, a mask shell adapted to output a gas to a respiratory system of a person, the mask shell adapted to be connected to the gas supply hose, and a gas flow volume regulating device which maintains a substantially constant gas flow volume out of the respiratory mask independent of an internal gas pressure inside the respiratory mask.

The above and other features and advantages of the present invention will be further understood from the following description of the preferred embodiment thereof, taken in conjunction with the accompanying drawings.

DETAILED DESCRIPTION OF THE PREFERRED EMBODIMENTS

Figure 1:
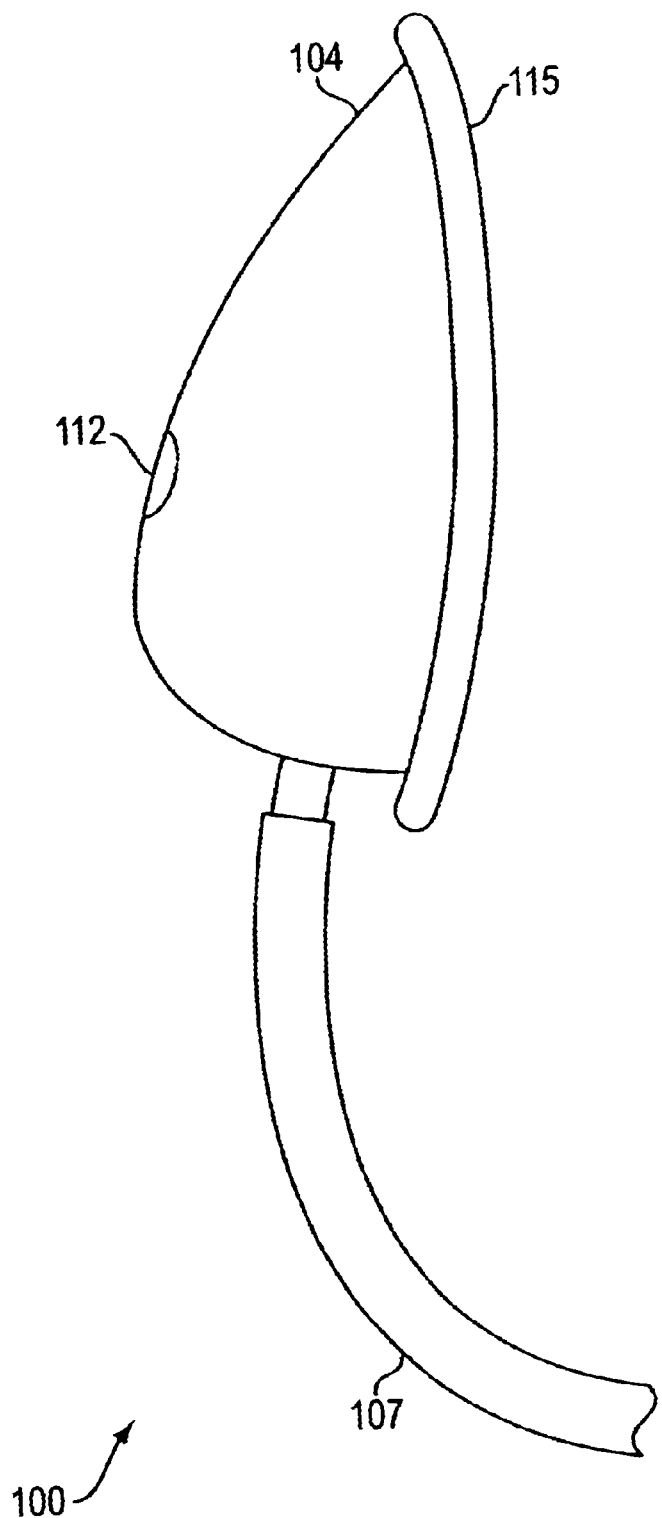
FIG. 1 shows a vented respiratory mask of the related art.
Figure 2:
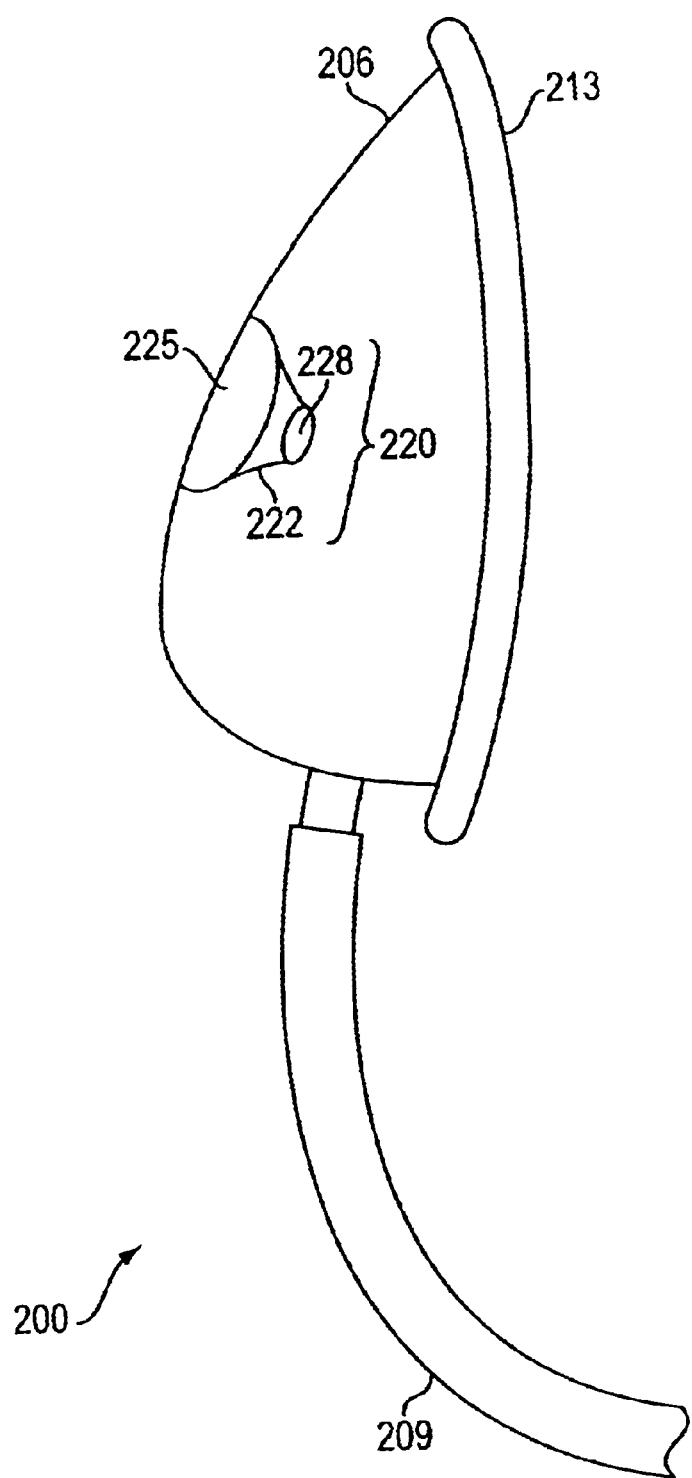
FIG. 2 shows a first embodiment of a variable aperture vented respiratory mask of the present invention.

FIG. 2 shows a first embodiment of a variable aperture vented respiratory mask 200 of the present invention. The variable aperture vented respiratory mask 200 includes a mask shell 206, a gas supply hose 209 attached to the mask shell 206, an optional gasket 213, and a gas flow volume regulating device 220. The gas flow volume regulating device 220 further includes a hollow elastomeric truncated cone 222 having an internal diameter, an outer aperture 225 in the mask shell 206, and an inner aperture 228 disposed inside the mask shell and forming a truncated end of the hollow elastomeric truncated cone 222. The gas flow volume regulating device 220 forms a variable aperture that responds to the internal pressure of the CPAP mask 200 in order to maintain a substantially constant gas flow volume out of the mask 200 regardless of pressure differences between the inside and the outside of the mask 200. In the preferred embodiment, the gas flow volume regulating device 220 is designed with aperture sizes such that the resulting gas flow volume is adequate at the lowest CPAP working pressure, which is typically a pressure of about three to four cm $H_2O$. In the preferred embodiment, a minimum gas flow volume ten to fifteen liters per minute at a pressure of four cm $H_2O$ air pressure is sufficient to vent the exhaled air from the mask 200. Suitable aperture sizes are dependent on the cross-sectional geometry and depth of the hole. For example, with a round aperture and a wall thickness of 0.05 inch, to achieve a flow rate of 10–15 liter/min, the aperture diameter can be 0.157 inch at 4 cm $H_2O$ pressure, and 0.101 inch at 18 cm $H_2O$ pressure. Aperture sizes can fall between these values for intermediate pressures.

In use, the variable aperture vented respiratory mask 200 receives a gas from the gas supply hose 209 at an essentially constant pressure. In the shown embodiment of FIG. 2, the exhaust gas flow is regulated by the deformation of the hollow elastomeric truncated cone 222. As the internal pressure in the mask 200 increases (i.e., during exhalation by the wearer), the hollow elastomeric truncated cone 222 is increasingly deformed, decreasing the internal diameter. By regulating the size of the vent aperture, a volume of gas escaping from the gas flow volume regulating device 220 is kept below an objectionable level. It should be understood that a gas flow volume regulating device of any of the embodiments is preferably located on the mask shell, but alternatively may be located near the mask or on the gas supply hose.

The gas flow volume regulating device 220 in this embodiment may be set to a desired flow volume by the choice of material composing the hollow elastomeric truncated cone 222, which can be, for example, silicone, polyurethane or the like.

Figure 3:
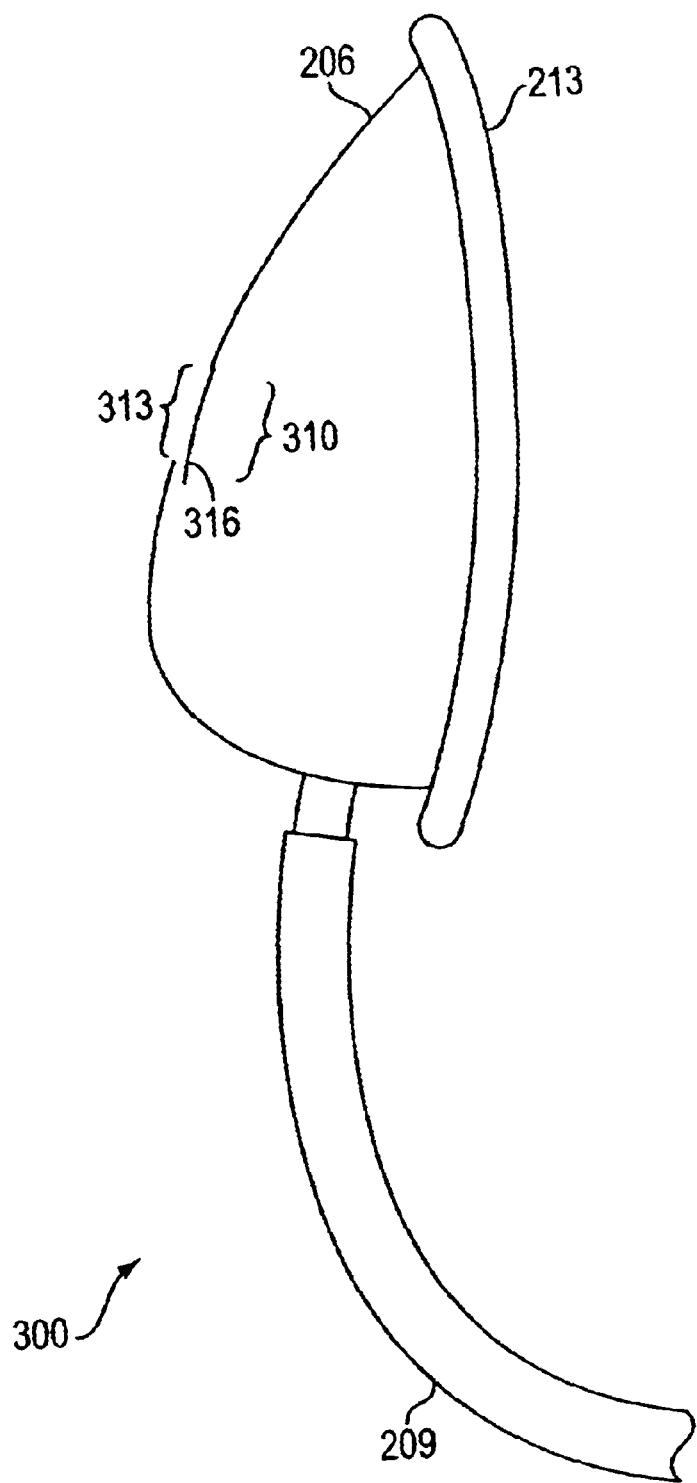
FIG. 3 shows a second embodiment of a variable aperture vented respiratory mask of the present invention.

FIG. 3 shows a second embodiment of a variable aperture vented respiratory mask 300. The main components are identical to the mask 220, and the reference numbers of the identical components are retained. The mask 300 includes a gas flow volume regulating device 310, which further includes an elastic flap 316 that is positioned over an aperture 313. The gas flow volume regulating device 310 therefore includes a variable aperture that responds to the internal pressure of the CPAP mask 300.

In a normal state, such as when the internal pressure is low, the elastic flap 313 is normally displaced away from he aperture 313, allowing an uninhibited gas flow through the aperture 313. As the internal pressure increases, the elastic flap 316 is displaced closer and closer to the aperture 313, regulating the gas flow volume through the aperture 313 and therefore regulating the internal pressure.

The gas flow volume regulating device 310 in this embodiment may be set to a desired flow volume by the choice of material composing the elastic flap 313, which can be, for example, silicone, polyurethane or the like. The closing pressure on the flap can be varied, depending on the hardness of the material from which it is made, and the flap geometry.

Figure 4:
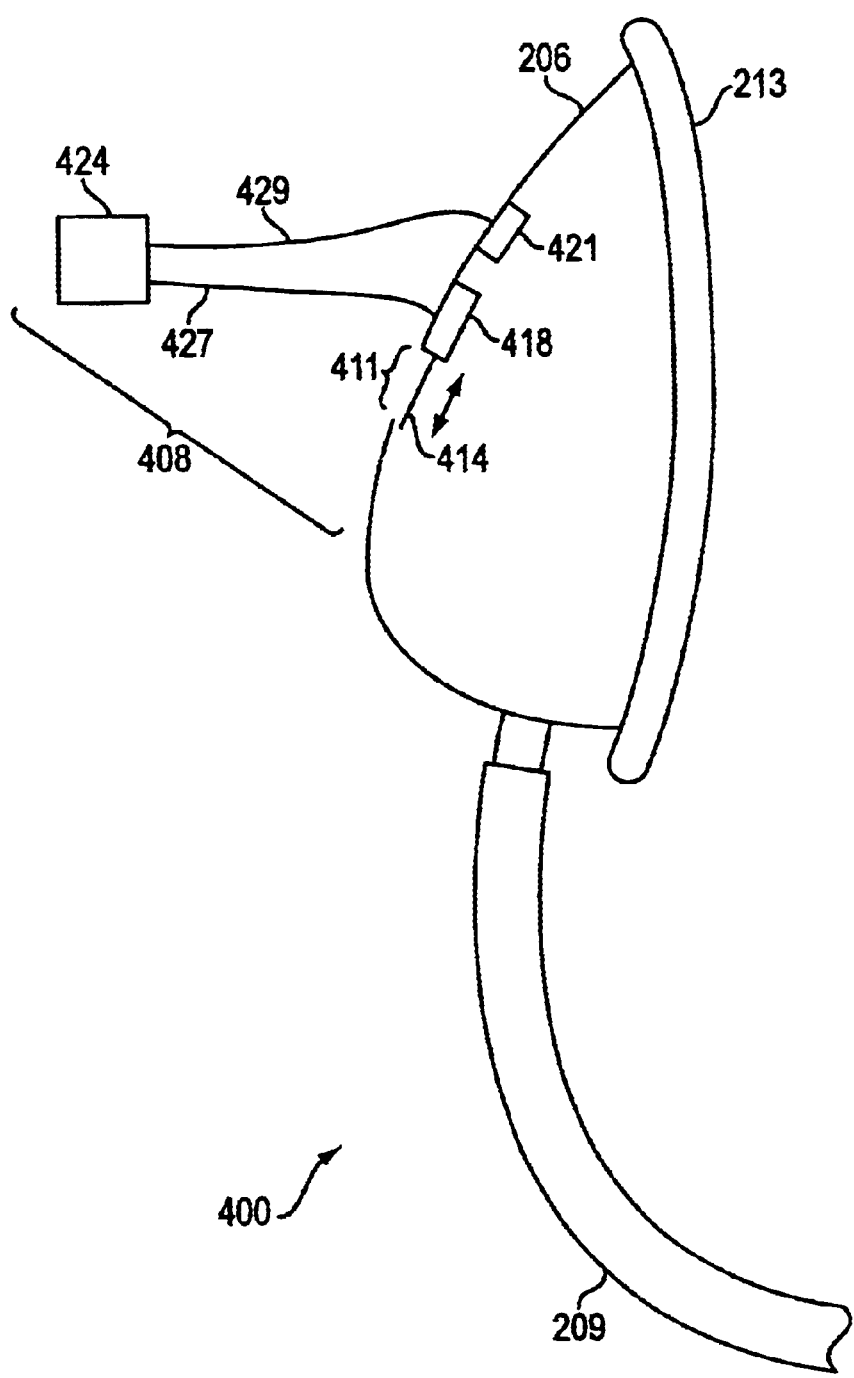
FIG. 4 shows a third embodiment of a variable aperture vented respiratory mask of the present invention.

FIG. 4 shows a third embodiment of a variable aperture vented respiratory mask 400. The main components are identical to the mask 200, and the reference numbers of the identical components are retained. The mask 400 includes a gas flow volume regulating device 408, which further includes an aperture 411, an electronically actuated member 414, an actuator 418, a pressure sensor 421, and a controller 424 connected to the actuator 418 by a control line 427 and to the pressure sensor 421 by a signal line 429. The gas flow volume regulating device 408 therefore includes a variable aperture that responds to the internal pressure of the mask 400.

The controller 424 may be any type of general purpose controller, including a programmable device such as a microcontroller, a custom-built chip, or a hard-wired logic circuit. The actuator 418 may be any type of general purpose actuator, such as a servo-type actuator or solenoid-type actuator. In the preferred embodiment, the actuator 418 is a servo-type actuator that extends and retracts the electronically actuated member 414 so as to cover or uncover the aperture 411. Alternatively, the actuator 418 may move the electronically actuated member 414 in some other manner, such as displacing it to a side of the aperture 411 or away from the aperture 411 into the interior of the mask shell 206.

In use, the controller 424 receives a pressure signal from the pressure sensor 421 over the signal line 429. The controller may then adjust the placement of the electronically actuated member 414 in relation to the aperture 411. The controller may do this by sending a control signal to the actuator 418 over the control line 427. The actuator, in response to the control signal, may move the electronically actuated member 414 to cover or uncover the aperture 411, thereby varying an effective size of the aperture 411. In the preferred embodiment, the electronically actuated member 414 may move anywhere from a fully covering position to a fully uncovering position and anywhere in between. Alternatively, the actuator 418 may have only covering and uncovering positions, with gas flow volume regulation being accomplished by repeatedly covering and uncovering the aperture 411.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A respiratory mask having a variable flow venting, comprising:
    a gas supply hose;
    a mask shell adapted to output a gas to a respiratory system of a person, said mask shell adapted to be connected to said gas supply hose; and
    a gas flow volume regulating device for substantially maintaining a substantially constant exhaust gas flow volume out of said respiratory mask independent of an internal gas pressure inside said respiratory mask,
    wherein said gas flow volume regulating device comprises a hollow elastomeric truncated cone, said hollow elastomeric truncated cone having an internal diameter, an outer aperture, and an inner aperture forming a truncated end of said hollow elastomeric truncated cone, with said hollow elastomeric truncated cone being deformable by a gas pressure within said respiratory mask to change said internal diameter of said hollow elastomeric truncated cone.

2. The respiratory mask of claim 1, wherein said gas flow volume regulating device is located on said mask shell.

3. The respiratory mask of claim 1, wherein said gas flow volume regulating device is located on said gas supply hose.

4. The respiratory mask of claim 1, wherein said gas flow volume regulating device maintains a gas flow volume of about ten to fifteen liters per minute.

5. A respiratory mask having a variable flow venting, comprising:
    a gas supply hose;
    a mask shell adapted to output a gas to a respiratory system of a person, said mask shell adapted to be connected to said gas supply hose; and
    a gas flow volume regulating device for substantially maintaining a substantially constant exhaust gas flow volume out of said respiratory mask independent of an internal gas pressure inside said respiratory mask,
    wherein said gas flow volume regulating device further comprises an actuator containing an electronically actuated member that is movable in relation to a vent aperture.

6. The respiratory mask of claim 5, wherein said gas flow volume regulating device is located on said mask shell.

7. The respiratory mask of claim 5, wherein said gas flow volume regulating device is located on said gas supply hose.

8. The respiratory mask of claim 5, wherein said gas flow volume regulating device maintains a gas flow volume of about ten to fifteen liters per minute.

9. A respiratory mask having a variable flow venting, comprising:
    a gas supply hose;
    a mask shell adapted to output a gas to a respiratory system of a person, said mask shell adapted to be connected to said gas supply hose; and
    a gas flow volume regulating device for substantially maintaining a substantially constant exhaust gas flow volume out of said respiratory mask independent of an internal gas pressure inside said respiratory mask,
    wherein said gas flow volume regulating device comprises an actuator containing an electronically actuated member that is movable in relation to a vent aperture and in response to said internal gas pressure.

10. The respiratory mask of claim 8, wherein said gas flow volume regulating device is located on said mask shell.

11. The respiratory mask of claim 9, wherein said gas flow volume regulating device is located on said gas supply hose.

12. The respiratory mask of claim 9, wherein said gas flow volume regulating device maintains a gas flow volume of about ten to fifteen liters per minute.

13. A respiratory mask having a variable flow venting, comprising:
    a gas supply hose;

a mask shell adapted to output a gas to a respiratory system of a person, said mask shell adapted to be connected to said gas supply hose; and a gas flow volume regulating device for substantially maintaining a substantially constant exhaust gas flow volume out of said respiratory mask independent of an internal gas pressure inside said respiratory mask, wherein said gas flow volume regulating device comprises:
- an actuator containing an electronically actuated member that is movable in relation to a vent aperture; and
- a pressure sensor.

14. The respiratory mask of claim 13, wherein said gas flow volume regulating device is located on said mask shell.

15. The respiratory mask of claim 13, wherein said gas flow volume regulating device is located on said gas supply hose.

16. The respiratory mask of claim 13, wherein said gas flow volume regulating device maintains a gas flow volume of about ten to fifteen liters per minute.

17. A respiratory mask having a variable flow venting, comprising:

a gas supply hose;

a mask shell adapted to output a gas to a respiratory system of a person, said mask shell adapted to be connected to said gas supply hose; and a gas flow volume regulating device for substantially maintaining a substantially constant exhaust gas flow volume out of said respiratory mask independent of an internal gas pressure inside said respiratory mask, wherein said gas flow volume regulating device comprises:
- an actuator containing an electronically actuated member that is movable in relation to a vent aperture;
- a pressure sensor; and
- a controller communicating with said actuator and said pressure sensor in order to vary an effective size of said vent aperture.

18. The respiratory mask of claim 17, wherein said gas flow volume regulating device is located on said mask shell.

19. The respiratory mask of claim 17, wherein said gas flow volume regulating device is located on said gas supply hose.

20. The respiratory mask of claim 17, wherein said gas flow volume regulating device maintains a gas flow volume of about ten to fifteen liters per minute.

* * * * *